(12) United States Patent
Berg et al.

(10) Patent No.: US 7,419,696 B2
(45) Date of Patent: Sep. 2, 2008

(54) MEDICAL DEVICES FOR DELIVERING A THERAPEUTIC AGENT AND METHOD OF PREPARATION

(75) Inventors: Eric P. Berg, Grapevine, TX (US);
Ronald J. Tuch, Plymouth, MN (US);
Michael Dror, Herzliya (IL); Rodney G. Wolff, Minnetonka Beach, MN (US)

(73) Assignee: Medtronic, Inc., Minneapolis, MN (US)

( * ) Notice: Subject to any disclaimer, the term of this patent is extended or adjusted under 35 U.S.C. 154(b) by 381 days.

(21) Appl. No.: 11/292,171

(22) Filed: Nov. 30, 2005

(65) Prior Publication Data

US 2006/0085064 A1 Apr. 20, 2006

Related U.S. Application Data

(60) Continuation of application No. 10/147,872, filed on May 20, 2002, now Pat. No. 6,997,949, which is a continuation of application No. 09/070,192, filed on Apr. 30, 1998, now abandoned, which is a continuation-in-part of application No. 08/728,541, filed on Oct. 9, 1996, now Pat. No. 5,776,184, which is a division of application No. 08/482,346, filed on Jun. 7, 1995, now Pat. No. 5,679,400, which is a continuation-in-part of application No. 08/052,878, filed on Apr. 26, 1993, now Pat. No. 5,464,650.

(51) Int. Cl.
*A61L 33/00* (2006.01)
*B05D 1/02* (2006.01)
*B05D 1/18* (2006.01)
*B05D 1/36* (2006.01)

(52) U.S. Cl. .................... 427/2.24; 427/2.14; 427/2.25; 427/2.28; 427/427.4; 427/372.2; 427/379

(58) Field of Classification Search .................. 427/2.1, 427/2.14, 2.24, 2.25, 2.28, 427/4, 372.2, 427/379
See application file for complete search history.

(56) References Cited

U.S. PATENT DOCUMENTS 3,105,492 A 10/1963 Jeckel (Continued)

FOREIGN PATENT DOCUMENTS

CH 649 916 A5 6/1985

(Continued)

OTHER PUBLICATIONS

Dyck, "Inorganic Heparin Complexes for the Preparation of Nonthrombogenic Surfaces," J. Biomed. Mater. Res., 6, pp. 115-141 (1972).

(Continued)

*Primary Examiner*—William P. Fletcher, III
*Assistant Examiner*—Cachet I Sellman (57) ABSTRACT

A method for making an intravascular stent by applying to the body of a stent a solution which includes a solvent, a polymer dissolved in the solvent and a therapeutic substance dispersed in the solvent and then evaporating the solvent. The inclusion of a polymer in intimate contact with a drug on the stent allows the drug to be retained on the stent during expansion of the stent and also controls the administration of drug following implantation. The adhesion of the coating and the rate at which the drug is delivered can be controlled by the selection of an appropriate bioabsorbable or biostable polymer and the ratio of drug to polymer in the solution. By this method, drugs such as dexamethasone can be applied to a stent, retained on a stent during expansion of the stent and elute at a controlled rate.

19 Claims, 3 Drawing Sheets

U.S. PATENT DOCUMENTS

| | | |
|---|---|---|
| 3,425,418 A | 2/1969 | Chvapil et al. |
| 3,451,996 A | 6/1969 | Sumyk et al. |
| 3,523,807 A | 8/1970 | Gerendas |
| 3,549,409 A | 12/1970 | Dyck |
| 3,688,317 A | 9/1972 | Kurtz |
| 3,717,502 A | 2/1973 | Masuhara et al. |
| 4,004,979 A | 1/1977 | Avrameas et al. |
| 4,118,449 A | 10/1978 | Rinde |
| 4,188,188 A | 2/1980 | Willner et al. |
| 4,229,540 A | 10/1980 | Coan |
| 4,229,838 A | 10/1980 | Mano |
| 4,265,928 A | 5/1981 | Braun |
| 4,292,965 A | 10/1981 | Nash et al. |
| 4,321,711 A | 3/1982 | Mano |
| 4,357,312 A | 11/1982 | Hsieh et al. |
| 4,459,317 A | 7/1984 | Lambert |
| 4,529,614 A | 7/1985 | Burns |
| 4,532,929 A | 8/1985 | Matei et al. |
| 4,540,573 A | 9/1985 | Neurath et al. |
| 4,548,736 A | 10/1985 | Muller et al. |
| 4,605,406 A | 8/1986 | Cahalan et al. |
| 4,605,564 A | 8/1986 | Kulla et al. |
| 4,612,337 A | 9/1986 | Fox, Jr. et al. |
| 4,613,665 A | 9/1986 | Larm |
| 4,623,539 A | 11/1986 | Tunc |
| 4,678,660 A | 7/1987 | McGary et al. |
| 4,680,177 A | 7/1987 | Gray et al. |
| 4,680,507 A | 7/1987 | Gray et al. |
| 4,733,665 A | 3/1988 | Palmaz |
| 4,740,207 A | 4/1988 | Kreamer |
| 4,749,585 A | 6/1988 | Greco et al. |
| 4,753,652 A | 6/1988 | Langer et al. |
| 4,762,128 A | 8/1988 | Rosenbluth |
| 4,768,507 A | 9/1988 | Fischell et al. |
| 4,770,664 A | 9/1988 | Gogolewski |
| 4,776,337 A | 10/1988 | Palmaz |
| 4,795,458 A | 1/1989 | Regan |
| 4,800,882 A | 1/1989 | Gianturco |
| 4,816,339 A | 3/1989 | Tu et al. |
| 4,842,575 A | 6/1989 | Hoffman, Jr. et al. |
| 4,869,909 A | 9/1989 | Takahashi et al. |
| 4,873,308 A | 10/1989 | Coury et al. |
| 4,886,062 A | 12/1989 | Wiktor |
| 4,888,009 A | 12/1989 | Lederman et al. |
| 4,893,623 A | 1/1990 | Rosenbluth |
| 4,894,231 A * | 1/1990 | Moreau et al. ............... 424/426 |
| 4,950,256 A | 8/1990 | Luther et al. |
| 4,955,893 A | 9/1990 | Yannas et al. |
| 4,955,899 A | 9/1990 | Della Corna et al. |
| 4,997,440 A | 3/1991 | Dumican |
| 5,010,063 A | 4/1991 | Piani et al. |
| 5,013,717 A | 5/1991 | Solomon et al. |
| 5,019,090 A | 5/1991 | Pinchuk |
| 5,019,096 A | 5/1991 | Fox, Jr. et al. |
| 5,037,377 A | 8/1991 | Alonso |
| 5,039,529 A | 8/1991 | Bergendal et al. |
| 5,041,100 A | 8/1991 | Rowland et al. |
| 5,059,166 A | 10/1991 | Fischell et al. |
| 5,061,276 A | 10/1991 | Tu et al. |
| 5,092,841 A | 3/1992 | Spears |
| 5,092,877 A | 3/1992 | Pinchuk |
| 5,102,402 A * | 4/1992 | Dror et al. .................. 604/265 |
| 5,102,417 A | 4/1992 | Palmaz |
| 5,104,860 A | 4/1992 | Piani et al. |
| 5,123,917 A | 6/1992 | Lee |
| 5,152,781 A | 10/1992 | Tang et al. |
| 5,176,907 A | 1/1993 | Leong |
| 5,192,308 A | 3/1993 | Ostapchenko |
| 5,195,984 A | 3/1993 | Schatz |
| 5,197,977 A | 3/1993 | Hoffman, Jr. et al. |
| 5,213,580 A | 5/1993 | Slepian et al. |
| 5,221,698 A | 6/1993 | Amidon et al. |
| 5,234,456 A | 8/1993 | Silvestrini |
| 5,242,391 A | 9/1993 | Place et al. |
| 5,282,823 A * | 2/1994 | Schwartz et al. ........... 623/1.22 |
| 5,290,266 A | 3/1994 | Rohling et al. |
| 5,295,978 A | 3/1994 | Fan et al. |
| 5,304,121 A | 4/1994 | Sahatjan |
| 5,306,250 A * | 4/1994 | March et al. ................. 604/104 |
| 5,342,605 A | 8/1994 | Illig |
| 5,352,434 A | 10/1994 | Illig et al. |
| 5,356,433 A | 10/1994 | Rowland et al. |
| 5,366,504 A | 11/1994 | Andersen et al. |
| 5,380,299 A | 1/1995 | Fearnot et al. |
| 5,399,381 A | 3/1995 | Mancilla et al. |
| 5,416,131 A | 5/1995 | Wolff et al. |
| 5,443,496 A | 8/1995 | Schwartz et al. |
| 5,447,724 A | 9/1995 | Helmus et al. |
| 5,451,424 A | 9/1995 | Solomon et al. |
| 5,464,650 A | 11/1995 | Berg et al. |
| 5,510,077 A | 4/1996 | Dinh et al. |
| 5,512,055 A | 4/1996 | Domb et al. |
| 5,531,735 A | 7/1996 | Thompson |
| 5,541,305 A | 7/1996 | Yokota et al. |
| 5,545,208 A | 8/1996 | Wolff et al. |
| 5,554,182 A | 9/1996 | Dinh et al. |
| 5,558,900 A | 9/1996 | Fan et al. |
| 5,571,166 A | 11/1996 | Dinh et al. |
| 5,578,075 A | 11/1996 | Dayton |
| 5,591,199 A | 1/1997 | Porter et al. |
| 5,591,227 A | 1/1997 | Dinh et al. |
| 5,599,352 A | 2/1997 | Dinh et al. |
| 5,605,676 A | 2/1997 | Eury et al. |
| 5,607,463 A * | 3/1997 | Schwartz et al. ........... 623/1.44 |
| 5,609,629 A | 3/1997 | Fearnot et al. |
| 5,624,411 A | 4/1997 | Tuch |
| 5,634,899 A | 6/1997 | Shapland et al. |
| 5,634,946 A | 6/1997 | Slepian |
| 5,679,400 A | 10/1997 | Tuch |
| 5,697,967 A | 12/1997 | Dinh et al. |
| 5,716,981 A | 2/1998 | Hunter et al. |
| 5,769,884 A | 6/1998 | Solovay |
| 5,776,184 A | 7/1998 | Tuch |
| 5,824,048 A | 10/1998 | Tuch |
| 5,848,995 A | 12/1998 | Walder |
| 6,013,099 A | 1/2000 | Dinh et al. |
| 6,146,358 A * | 11/2000 | Rowe .................... 604/103.02 |
| 6,187,370 B1 | 2/2001 | Dinh et al. |
| 6,203,536 B1 | 3/2001 | Berg et al. |
| 6,399,144 B2 | 6/2002 | Dinh et al. |
| 6,716,444 B1 | 4/2004 | Castro et al. |

FOREIGN PATENT DOCUMENTS

| | | |
|---|---|---|
| CH | 649916 A5 | 6/1985 |
| EP | 0366564 A2 | 5/1990 |
| EP | 0 815 806 A2 | 1/1998 |
| EP | 815806 A2 | 1/1998 |
| FR | 2035774 | 12/1970 |
| WO | WO 86/06729 | 11/1986 |
| WO | WO 87/03495 A1 | 6/1987 |
| WO | WO 89/07932 | 9/1989 |
| WO | WO 90/03332 | 11/1990 |
| WO | WO 91/12779 | 9/1991 |
| WO | WO 91/16102 | 10/1991 |
| WO | WO 91/17724 A1 | 11/1991 |
| WO | WO 91/17744 | 11/1991 |
| WO | WO 91/17789 | 11/1991 |
| WO | WO 91/18940 | 12/1991 |
| WO | WO 92/15286 | 9/1992 |
| WO | WO 92/21387 A1 | 12/1992 |
| WO | WO 93/06792 | 4/1993 |
| WO | WO 94/17108 | 8/1994 |
| WO | WO 94/27612 | 12/1994 |

| WO | WO 95/03083 | 2/1995 |
| WO | WO 95/03085 | 2/1995 |
| WO | WO 95/10989 | 4/1995 |
| WO | WO 96/32907 | 10/1996 |
| WO | WO 97/07973 | 3/1997 |
| WO | WO 97/10011 | 3/1997 |
| WO | WO 97/42911 | 11/1997 |
| WO | WO 99/16386 | 4/1999 |

OTHER PUBLICATIONS

Lincoff et al., "Intracoronary Stenting Compared with Conventional Therapy for Abrupt Vessel Closure Complicating Coronary Angioplasty," J.Am. Coll. Cardio., 21, pp. 866/857, (1993).

Spotnitz et al., "Fibrin Glue from Stored Human Plasma. An Inexpensive and Efficient Method for Local Blood Bank Preparation," The American Surgeon, 53, 460-462 (1987).

Van Beusekom et al., "Synthetic Polymers as an Alternative to metal in Stents? In Vivo and Mechanical Behavior of Polyethylene-Terephtalate," Circulation, 86 (supp. 1), pp. 1-731, No. 2912, 1992.

K. Whang et al. "A Novel Method to Fabricate Bioabsorable Scaffold," Polymer, 36:4, 837-842 (1995).

Liu et al. "Porous Polyurethane Vascular Prostheses With Variable Compliance," J. Biomed. Mater. Res., 26, pp. 1489 (1192).

McNair, "Using Hydrogel Polymers for Drug Delivery," Medical Device Technology, pp. 16-22, (1996).

"Photolink Surface Modifications Technical Bulletin: Heparin Coatings for Medical Devices," Brochure from BSI Surface Modifications Sciences, (1994).

D. Cox et al. "Local Delivery of heparin and Methotrexate Fails to Inhibit in Vivo Smooth Muscle Cell Proliferation" Supplement to Circulation, vol. 84, No. 4, pp. 0284, Oct. 1991.

M. Ebecke, et al. "In Vitro Assessment of Polyactides as Slow Release Drug Carriers", Supplement to Circulation, vol. 84, No. 4, pp. 0285, Oct. 1991.

S. Bailey et al. "Heparin Coating of Endovascular Stents Decreases Subacute Thrombosis in a Rabbit Model," Supplement to Circulation, vol. 86, No. 4, pp. 0741, Oct. 1992.

European Appeal Document for EP 0 623 354, Response to Grounds of Appeal with copies of the Annex and auxiliary requests, submitted by Medtronic, Inc., 65 pages, filed Nov. 24, 2006.

European Appeal Document for EP 0 623 354, Grounds of Appeal, submitted by Advanced Cardiovacular Systems, Inc., 20 pages, filed May 8, 2006.

European Appeal Document for EP 0 623 354, Notice of Appeal from the Decision maintaining EP Patent No. 0 623 354, submitted by Advanced Cardiovascular Systems, Inc., 2 pages, filed Feb. 28, 2006.

European Opposition Document for EP 0 623 354, Interlocutory decision in Opposition proceedings (Articles 102(3) and 106(3) EPC), 25 pages, dated December 27, 2005.

European Opposition Document for EP 0 623 354, Provision of a copy of the minutes in accordance with Rule 76(4) EPC, 8 pages, dated Dec. 27, 2005.

European Opposition Document for EP 0 623 354, Information regarding the Oral Proceedings of Nov. 9, 2005, 1 page, dated Nov. 9, 2005.

European Opposition Document for EP 0 623 354, Minutes of the Oral Proceedings before the Opposition Division with Annexes, 14 pages, dated Nov. 9, 2005.

European Opposition Document for EP 0 623 354, Response to Summons to Attend Oral Proceedings, submitted by Advanced Cardiovascular Systems, Inc., 2 pages, filed Sep. 9, 2005.

European Opposition Document for EP 0 623 354, Patentee's Response to Summons to Attend Oral Proceedings with Auxiliary Request I to XI, submitted by Medtronic, Inc., 64 pages, filed Sep. 8, 2005.

European Opposition Document for EP 0 623 354, Summons to Attend Oral Proceedings Pursuant to Rule 71(1) EPC with annexes, 6 pages dated Feb. 22, 2005.

European Opposition Document for EP 0 623 354, Opponent's Comments to Patentee's Response, 8 pages, filed Jul. 29, 2004.

European Opposition Document for EP 0 623 354, Patentee's Response to the Notice of Opposition, submitted by Medtronic Inc., 25 pages, filed Apr. 16, 2004.

European Opposition Document for EP 0 623 354, Notice of Opposition with Form 2300 and Annex, submitted by Advanced Cardiovascular Systems, Inc., 15 pages, filed Jul. 2, 2003.

European Prosecution Document for EP 0 623 354, Patentee's Response to the European Official Action pursuant to Article 96(2) and Rule 51(2) EPC, 3 pages, filed Jul. 9, 1998.

Response to Office Action for Related U.S. Appl. No. 08/482,346, inventor Tuch, R.J., 7 pages, filed Jul. 26, 1996.

Alvarado, R., et al., "Evaluation of Polymer-coated Balloon-expandable Stents in Bile Ducts," Radiology 170:975-978, Radiological Society of North America (1989).

Badger Air-Brush Co., Badger, Model 200, Air-Brush Instruction Book, 12 pages, Badger Air-Brush Co. (Oct. 1994).

Badger Air-Brush Co., Pinceau Pneumatique Badger Modele No 200, Livret D'Instructions Pour Utiliser le Pinceau Pneumatique, 8 pages, Badger Air-Brush Co.

Badger Air-Brush Co., Badger basic Spray Gun Instruction Book, 4 pages, Badger Air-Brush Co.

Badger Air-Brush Co., Badger Model 200, Air-Brush Instruction Book, 12 pages, Badger Air-Brush Co. (Oct. 2005).

Becker, G.J., et al., "Percutaneous Placement of a Ballon-expandable Intraluminal Graft for Life-threatening Subclavian Arterial Hemorrhage," J. Vasc. Interventional Radiol. 2:225-229, Society of Cardiovascular and Interventional Radiology (1991).

Block, P.C., "Coronary-Artery Stents and Other Endoluminal Devices," New Engl. J. Med. 324:52-53, Massachusetts Medical Society (1991).

Bonan, R., et al., "Coronary artery stenting after angioplasty with self-expanding parallel wire metallic stents," Am. Heart J. 121:1522-1530, Mosby-Year Book, Inc. (1991).

Cavender, J.B., et al., "The Effects of Heparin Bonded Tantalum Stents on Thrombosis and Neointimal Proliferation," Circulation Suppl. 82:III-541, Abstract No. 2149, American Heart Association (1990).

Charnsangavej, C., et al., "Endovascular Stent for Use in Aortic Dissection: An in Vitro Experiment," Radiology 157:323-324, Radiology Society of North American (1985).

Chen, M.-C., et al., "A novel drug-eluting stent spray-coated with multi-layers of collagen and sirolimus," J. Contr. Rel. 108:178-189, Elsevier B.V. (Nov. 2005).

Cragg, A.H., et al., "Percutaneous Arterial Grafting," Radiology 150:45-49, Radiological Society of North America (1984).

Cragg, A.H., et al., "Nitinol Intravascular Stent: Results of Preclinical Evaluation," Radiology 189:775-778, Radiological Society of North America (Dec. 1993).

Cragg, A.H., et al., "Percutaneous Femoropopliteal Graft Placement," J. Vasc. Interventional Radiol. 4:455-463, Society of Cardiovascular and Interventional Radiology (Jul.-Aug. 1993).

de Scheerder, I., et al., "Local methylprednisolone inhibition of foreign body response to coated intracoronary stents," Cor. Art. Dis. 7:161-166, Lippincott, Williams & Wilkins (Feb. 1996).

Dotter, C.T., "Transluminally placed Coilspring Endarterial Tube Grafts," Invest. Radiol. 4:329-332, Lippincott, Williams & Wilkins (1969).

Dotter, C.T., et al., "Transluminal Expandable Nitinol Coil Stent Grafting: Preliminary Report," Radiol. 147:259-260, Radiological Society of North America (1983).

European Opposition Document for EP 0 623 354, Declaration of Shaul M. Aharoni, submitted by Advanced Vascular Systems, Inc., 3 pages, submitted Sep. 9, 2005.

European Opposition Document for EP 0 623 354, Curriculum Vitae of Shaul M. Aharoni, submitted by Advanced Vascular Systems, Inc., 1 page, submitted Sep. 9, 2005.

European Appeal Document for EP 0 623 354, Declaration of Kenneth W. Schlotfeldt, submitted by Advanced Vascular Systems, Inc., 2 pages, submitted May 9, 2006.

European Opposition Document for EP 0 623 354, Declaration of Dr. Arina van Breda, M.D., submitted by Medtronic Inc., 17 pages, submitted Sep. 8, 2005.

European Opposition Document for EP 0 623 354, Curriculum Vitae of Dr. Arina van Breda, M.D., submitted by Medtronic Inc.., 17 pages, submitted Sep. 8, 2005.

Fischman, D., et al., "Overview of the Palmaz-Schatz™ Stent," *J. Invas. Cardiol.* 3:75-84, HMP Communications (1991).

George, P.J.M., et al., "Covered expandable metal stent for recurrent tracheal obstruction," *Lancet 335*:582-584, Lippincott, Williams & Wilkins (1990).

Lambert, T., et al., "A New Method for Arterial Drug Delivery Via Removal Stent," *J. Am. Coll. Cardiol. Suppl A*. 21:483A, Abstract No. 834-2, Elsevier Biomedical (Feb. 1993).

Lambert, T.L., et al., "Localization Arterial Wall Drug Delivery From a Polymer-Coated Removable Metallic Stent," *Circulation 90*:1003-1011, American Heart Association (Aug. 1994).

Matco Tools Corporation, *Hobby and Touch-Up Air-Brush, Replacement Parts Operating Instructions Cleaning*, Model No. 200-1, 7 pages, Matco Tools Corporation.

Mobin-Uddin, K., et al., "Caval Interruption for Prevention of Pulmonary Embolism," *Arch. Surg.* 99:711-715, American Medical Association Publication (1969).

Mullins, C.E., et al., "Implantation of balloon-expandable intravascular grafts by catheterization in pulmonary arteries and systemic veins," *Circulation 77*:188-199, American Heart Association (1988).

Palmaz, J.C., "Expandable Vascular Endoprosthesis," *Research Project Report*, 9 pages, University of California (1983).

Palmaz, J.C., "Expandable Intraluminal Graft: A Preliminary Study," *Radiology 156*:73-77, Radiological Society of North America (1985).

Palmaz, J.C., et al., "Atherosclerotic Rabbit Aortas: Expandable Intraluminal Grafting," *Radiology 160*:723-726, Radiological Society of North America (1986).

Palmaz, J.C., et al., "Expandable intraluminal vascular graft: A feasibility study," *Surgery 99*:199-205, C.V. Mosby Co. (1986).

Palmaz, J.C., et al., "Normal and Stenotic Renal Arteries: Experimental Balloon-expandable Intraluminal Stenting," *Radiology 164*:705-708, Radiological Society of North America (1987).

Palmaz, J.C., "Balloon-Expandable Intravascular Stent," *Am. J. Roentgenol.* 150:1263-1269, American Roentgen Ray Society (1988).

Schatz, R.A., "A View of Vascular Stents," *Circulation 79*:445-457, American Heart Association (1989).

Schatz, R.A., et al., "Balloon-expandable intracoronary stents in the adult dog," *Circulation 76*:450-457, American Heart Association (1987).

Shin, J.H., et al., "Influence of a dexamethasone-eluting covered stent on tissue reaction: an experimental study in a canine bronchial model," *Eur. Radiol.* 15:1241-1249, Springer International (published online Jan. 2005).

Sigwart, U., et al., "Intravascular Stents to Prevent Occlusion and Restenosis After Transluminal Angioplasty," *New Eng. J. Med.* 316:701-706, Massachusetts Medical Society.

Van der Geissen, W.J., et al., "Self-expandable Mesh Stents: an Experimental Study comparing Polymer Coated and Uncoated Wallstent Stents in the Coronary Circulation of Pigs," *Circulation Suppl. III* 82:III-542, Abstract No. 2150, American Heart Association (1990).

Wright, K.C., et al., "Percutaneous Endovascular Stents: An Experimental Evaluation," *Radiol.* 456:69-72, Radiological Society of North America (1985).

Wright, K.C., et al., "Occlusive Effect of Metallic Stents on Canine Ureters," *Cardiovasc Intervent. Radiol.* 16:230-234, Springer International (Jul./Aug. 1993).

Zidar, J.P., et al., "In Vitro Thrombogenicity Analysis of a new Bioabsorbable, Balloon-expandable, Endovascular Stent," *J. Coll. Cardiol. Suppl.* 21:483A, Abstract No. 834-5, Elsevier Biomedical (Feb. 1993).

Espacenet, English language abstract of CH 649916, 1 page (document FP2 listed on accompanying PTO/SB/08A).

* cited by examiner

MEDICAL DEVICES FOR DELIVERING A THERAPEUTIC AGENT AND METHOD OF PREPARATION

RELATED APPLICATIONS

This application is a Continuation of U.S. application Ser. No. 10/147,872, filed May 20, 2002, which is a Continuation of U.S. application Ser. No. 09/070,192, filed Apr. 30, 1998, now abandoned, which is a Continuation-in-Part of Ser. No. 08/728,541, filed Oct. 9, 1996, now U.S. Pat. No. 5,776,184, which is a Divisional of U.S. application Ser. No. 08/482,346, filed Jun. 7, 1995, now U.S. Pat. No. 5,679,400, which is a Continuation-in-Part of U.S. application Ser. No. 08/052,878, filed Apr. 26, 1993, now U.S. Pat. No. 5,464,650, all of which are incorporated herein by reference.

BACKGROUND OF THE INVENTION

Field of the Invention

This invention relates to a medical device employing a therapeutic agent as a component thereof. For example, in an arterial site treated with percutaneous transluminal coronary angioplasty therapy for obstructive coronary artery disease a therapeutic antithrombogenic substance such as heparin may be included with a device and delivered locally in the coronary artery. Also provided is a method for making a medical device capable of localized application of therapeutic agents.

Medical devices which serve as substitute blood vessels, synthetic and intraocular lenses, electrodes, catheters, and the like, in and on the body, or as extracorporeal devices intended to be connected to the body to assist in surgery or dialysis are well known. For example, intravascular procedures can bring medical devices into contact with the patient's vasculature. In treating a narrowing or constriction of a duct or canal percutaneous transluminal coronary angioplasty (PTCA) is often used with the insertion and inflation of a balloon catheter into a stenotic vessel. Other intravascular invasive therapies include atherectomy (mechanical systems to remove plaque residing inside an artery), laser ablative therapy, and the like. However, this use of mechanical repairs can have adverse consequences for the patient. For example, restenosis at the site of a prior invasive coronary artery disease therapy can occur. Although angioplasty procedures have increased greatly in popularity for treatment of occluded arteries, the problem of restenosis following the angioplasty treatment remains a significant problem. Restenosis is the closure of a peripheral or coronary artery following trauma to the artery caused by efforts to open an occluded portion of the artery by angioplasty, such as, for example, by balloon dilation, atherectomy or laser ablation treatment of the artery. For these angioplasty procedures, restenosis occurs at a rate of about 30-60% depending upon the vessel location, lesion length and a number of other variables. Restenosis, defined angiographically, is the recurrence of a 50% or greater narrowing of a luminal diameter at the site of a prior coronary artery disease therapy, such as a balloon dilatation in the case of PTCA therapy. In particular, an intra-luminal component of restenosis develops near the end of the healing process initiated by vascular injury, which then contributes to the narrowing of the luminal diameter. This phenomenon is sometimes referred to as "intimal hyperplasia." It is believed that a variety of biologic factors are involved in restenosis, such as the extent of the injury, platelets, inflammatory cells, growth factors, cytokines, endothelial cells, smooth muscle cells, and extracellular matrix production, to name a few.

Attempts to inhibit or diminish restenosis often include additional interventions such as the use of intravascular stents and the intravascular administration of pharmacological therapeutic agents. One aspect of restenosis may be simply mechanical; e.g. caused by the elastic rebound of the arterial wall and/or by dissections in the vessel wall caused by the angioplasty procedure. These mechanical problems have been successfully addressed by the use of stents to tack-up dissections and prevent elastic rebound of the vessel, thereby reducing the level of restenosis for many patients. The stent is typically inserted by catheter into a vascular lumen and expanded into contact with the diseased portion of the arterial wall, thereby providing internal support for the lumen. Examples of stents which have been successfully applied over a PTCA balloon and radially expanded at the same time as the balloon expansion of an affected artery include the stents disclosed in U.S. Pat. Nos. 4,733,665 (Palmaz), 4,800,882 (Gianturco), and 4,886,062 (Wiktor).

Also, such stents employing therapeutic agents such as glucocorticoids (e.g. dexamethasone, beclamethasone), heparin, hirudin, tocopherol, angiopeptin, aspirin, ACE inhibitors, growth factors, oligonucleotides, and, more generally, antiplatelet agents, anticoagulant agents, antimitotic agents, antioxidants, antimetabolite agents, and anti-inflammatory agents have been considered for their potential to solve the problem of restenosis. Such substances have been incorporated into (or onto) stents by a variety of mechanisms. These mechanisms involve incorporating the therapeutic agents into polymeric coatings and films, including hydrogels, as well as covalently binding the therapeutic agents to the surface of the stent.

For example, therapeutic agents have been dissolved or dispersed in a solution of polymer in an organic solvent. This is then sprayed onto the stent and allowed to dry. Alternatively, therapeutic agents have been incorporated into a solid composite with a polymer in an adherent layer on a stent body with fibrin in a separate adherent layer on the composite to form a two layer system. The fibrin is optionally incorporated into a porous polymer layer in this two layer system. The therapeutic agent, however, is incorporated into the underlying solid polymer. The overlying porous polymer layer provides a porous barrier through which the therapeutic agent is transferred.

Conventional methods of loading the therapeutic agent into a polymer, such as spray coating, do not provide high concentrations of therapeutic agents. Typically, upon spray coating a therapeutic agent onto a stent body, only about 2 percent of the spray is captured by the stent. This can be prohibitively expensive for therapeutic agents that are extremely costly and scarce, such as peptidic drugs.

Thus, what is needed is a medical device, preferably, a stent, having a porous polymeric material, typically a polymer layer in the form of a coating or film, with a therapeutic agent incorporated therein at sufficiently high concentrations that the therapeutic agent can be delivered over an extended period of time. Improved methods by which the therapeutic agent can be incorporated into the porous polymeric material with lower levels of waste are also needed.

This invention also relates to intravascular stents for treatment of injuries to blood vessels and particularly to stents having a framework onto which a therapeutic substance or drug is applied.

Metal stents such as those disclosed in U.S. Pat. No. 4,733,665 issued to Palmaz, U.S. Pat. No. 4,800,882 issued to Gianturco or U.S. Pat. No. 4,886,062 issued to Wiktor could be suitable for drug delivery in that they are capable of maintaining intimate contact between a substance applied to the outer surface of the stent and the tissues of the vessel to be treated. However, there are significant problems to be overcome in order to secure a therapeutically significant amount of a substance onto the metal of the stent; to keep it on the stent during expansion of the stent into contact with the blood vessel wall; and also controlling the rate of drug delivery from the drug on the stent to the vessel wall.

It is therefore another object of the present invention to provide a stent having a therapeutically significant amount of a drug applied thereto.

It is also an object of the present invention to provide a stent which may be delivered and expanded in a selected blood vessel without losing a therapeutically significant amount of a drug applied thereto.

It is also an object of the present invention to provide a drug-containing stent which allows for a sustained release of the drug to vascular tissue.

It is also an object of the present invention to provide a simple method for applying to a stent a coating of a therapeutic substance.

SUMMARY OF THE INVENTION

This invention relates to a medical device having a porous polymeric material with a therapeutic agent therein. Preferably, the device according to the invention is capable of applying a highly localized therapeutic agent into a body lumen to treat or prevent injury. The term "injury" means a trauma, that may be incidental to surgery or other treatment methods including deployment of a stent, or a biologic disease, such as an immune response or cell proliferation caused by the administration of growth factors. In addition, the methods of the invention may be performed in anticipation of "injury" as a prophylactic. A prophylactic treatment is one that is provided in advance of any symptom of injury in order to prevent injury, prevent progression of injury or attenuate any subsequent onset of a symptom of such injury.

In accordance with the invention, a device for delivery of localized therapeutic agent includes a structure including a porous material and an elutable (i.e., capable of being dissolved under physiological conditions) therapeutic agent in the form of a solid, gel, or neat liquid, which is dispersed throughout at least a portion, and preferably a substantial portion, of the porous material. Preferably, the device is capable of being implanted in a body so that the localized therapeutic agent can be delivered in vivo, typically at a site of vascular injury or trauma. Preferably, the porous material is biocompatible, sufficiently tear-resistant, and nonthrombogenic.

The porous material may be a layer (e.g., a film, i.e., a sheet material or a coating) on at least a portion of the structure. Alternatively, the porous material may be an integral portion of the structure. Preferably, the porous material is a polymeric material selected from the group of a natural hydrogel, a synthetic hydrogel, silicone, polyurethane, polysulfone, cellulose, polyethylene, polypropylene, polyamide, polyester, polytetrafluoroethylene, and a combination of two or more of these materials. Examples of natural hydrogels include fibrin, collagen, elastin, and the like. More preferably, the porous polymeric material is a nonswelling biostable polymer selected from the group of silicone, polyurethane, polysulfone, cellulose, polyethylene, polypropylene, polyamide, polyester, polytetrafluoroethylene, and a combination of two or more of these materials.

The therapeutic agent can be one or more of a wide variety of therapeutic agents, including peptidic drugs. Preferably, the therapeutic agent includes an antithrombotic material. More preferably, the antithrombotic material is a heparin or heparin derivative or analog. Such therapeutic agents are soluble in water such that they elute from the porous polymeric material.

The structure of the device can be adapted for its intended extracorporeal or intravascular purpose in an internal human body site, such as an artery, vein, urethra, other body lumens, cavities, and the like or in an extracorporeal blood pump, blood filter, blood oxygenator or tubing. In one aspect of the invention, the shape is preferably generally cylindrical, and more preferably, the shape is that of a catheter, a stent, or a guide wire. In particularly preferred embodiments, the medical device is an intralumenal stent.

The invention also provides methods for making a medical device which includes therapeutic agents. In one embodiment, a method of the invention includes: providing a structure comprising a porous material; contacting the structure comprising a porous material with a concentrating agent to disperse the concentrating agent throughout at least a portion of the porous material; contacting the structure comprising a porous material and the concentrating agent with a solution of a therapeutic agent; and removing the therapeutic agent from solution within the porous material at the locations of the concentrating agent.

The present invention also provides a method for making a medical device that includes: providing a structure comprising a porous material; immersing the structure comprising a porous material in a saturated solution of a therapeutic agent for a sufficient period of time to allow the solution to fill the porous material; removing the medical device from the solution; drying the medical device; and repeating the steps of immersing, removing, and drying to provide a therapeutic agent dispersed within the porous material. Preferably, the method further includes a step of removing air bubbles from the porous material while being immersed in the solution of the therapeutic agent. The step of removing air bubbles from the porous material can include applying ultrasonics, reduced pressure, elevated pressure, or a combination thereof, to the solution. Preferably, the method involves loading a stent having a porous polymeric film thereon, and subsequently applying an overlayer of a polymer.

A therapeutic agent may be loaded onto a structure including a porous material at any number of points between, and including, the point of manufacture and the point of use. For example, the device can be stored and transported prior to incorporation of the therapeutic agent. Thus, the end user can select the therapeutic agent to be used from a wider range of therapeutic agents.

We have discovered a method for making an intravascular stent by applying to the body of a stent, and in particular to its tissue-contacting surface, a solution which includes a solvent, a polymer dissolved in the solvent and a therapeutic substance dispersed in the solvent and then evaporating the solvent. The inclusion of a polymer in intimate contact with a drug on the stent allows the drug to be retained on the stent in a resilient matrix during expansion of the stent and also slows the administration of drug following implantation. The method can be applied whether the stent has a metallic or polymeric surface. The method is also an extremely simple method since it can be applied by simply immersing the stent into the solution or by spraying the solution onto the stent. The amount of drug to be included on the stent can be readily controlled by applying multiple thin coats of the solution while allowing it to dry between coats. The overall coating should be thin enough so that it will not significantly increase the profile of the stent for intravascular delivery by catheter. It is therefore preferably less than about 0.002 inch thick and most preferably less than 0.001 inch thick. The adhesion of the coating and the rate at which the drug is delivered can be controlled by the selection of an appropriate bioabsorbable or biostable polymer and by the ratio of drug to polymer in the solution. By this method, drugs such as glucocorticoids (e.g. dexamethasone, betamethasone), heparin, hirudin, tocopherol, angiopeptin, aspirin, ACE inhibitors, growth factors, oligonucleotides, and, more generally, antiplatelet agents, anticoagulant agents, antimitotic agents, antioxidants, antimetabolite agents, and anti-inflammatory agents can be applied to a stent, retained on a stent during expansion of the stent and elute the drug at a controlled rate. The release rate can be further controlled by varying the ratio of drug to polymer in the multiple layers. For example, a higher drug-to-polymer ratio in the outer layers than in the inner layers would result in a higher early dose which would decrease over time.

In operation, the stent made according to the present invention can deliver drugs to a body lumen by introducing the stent transluminally into a selected portion of the body lumen and radially expanding the stent into contact with the body lumen. The transluminal delivery can be accomplished by a catheter designed for the delivery of stents and the radial expansion can be accomplished by balloon expansion of the stent, by self-expansion of the stent, or a combination of self-expansion and balloon expansion.

DESCRIPTION OF PREFERRED EMBODIMENTS

One of the more preferred configurations for a device according to the invention is a stent for use in artery/vascular therapies. The term "stent" refers to any device capable of being delivered by a catheter and which, when placed into contact with a portion of a wall of a lumen to be treated, will also deliver localized therapeutic agent at a luminal or blood-contacting portion of the device. A stent typically includes a lumen wall-contacting surface and a lumen-exposed surface. Where the stent is shaped generally cylindrical or tube-like, including a discontinuous tube or ring-like structure, the lumen-wall contacting surface is the surface in close proximity to the lumen wall whereas the lumen-exposed surface is the inner surface of the cylindrical stent. The stent can include polymeric or metallic elements, or combinations thereof, onto which a porous material is applied. For example, a deformable metal wire stent is useful as a stent framework of this invention, such as that described in U.S. Pat. No. 4,886,062 (Wiktor), which discloses preferred methods for making a wire stent. Other metallic stents useful in this invention include those of U.S. Pat. Nos. 4,733,655 (Palmaz) and 4,800,882 (Gianturco).

Other medical devices, such as heart valves, vascular grafts, pacing leads, etc., can also include the embodiments of the present invention. As used herein, medical device refers to a device that has surfaces that contact tissue, blood, or other bodily fluids in the course of their operation, which fluids are subsequently used in patients. This can include, for example, extracorporeal devices for use in surgery such as blood oxygenators, blood pumps, blood sensors, tubing used to carry blood and the like which contact blood which is then returned to the patient. This can also include endoprostheses implanted in blood contact in a human or animal body such as vascular grafts, stents, pacemaker leads, heart valves, and the like that are implanted in blood vessels or in the heart. This can also include devices for temporary intravascular use such as catheters, guide wires, and the like which are placed into the blood vessels or the heart for purposes of monitoring or repair.

Figure 1:
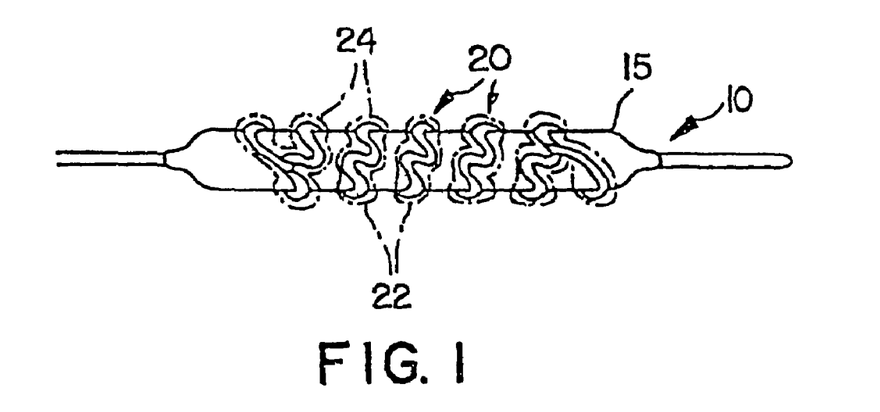
FIG. 1 is an elevational view of one embodiment of a device according to the invention with a balloon catheter as a mode of delivery of the device.

Referring now to FIG. 1, the stent 20 comprises a stent framework 22 and a porous material coating 24. The stent framework 22 is deformable and can be formed from a polymeric material, a metal, or a combination thereof. A balloon 15 is positioned in FIG. 1 adjacent the lumen-exposed surface of the stent to facilitate delivery of the stent. The stent 20 can be modified to increase or to decrease the number of wires provided per centimeter in the stent framework 22. Similarly, the number of wire turns per centimeter can also be modified to produce a stiffer or a more flexible stent framework.

Polymeric stents can also be used in this invention. The polymers can be nonbioabsorbable or bioabsorbable in part, or total. Stents of this invention can be completely nonbioabsorbable, totally bioabsorbable or a composite of bioabsorbable polymer and nonabsorbable metal or polymer. For example, another stent suitable for this invention includes the self-expanding stent of resilient polymeric material as disclosed in International Publication No. WO 91/12779 (Medtronic, Inc.).

Nonbioabsorbable polymers can be used as alternatives to metallic stents. The stents of this invention should not substantially induce inflammatory and neointimal responses. Examples of biostable nonabsorbable polymers that have been used for stent construction with or without metallic elements include polyethylene terephthalate (PET), polyurethane urea, and silicone. Although the porous material is shown as a coating 24, it is to be understood that, for the purposes of this invention, the porous material can be incorporated into the material of the stent.

Figure 2:
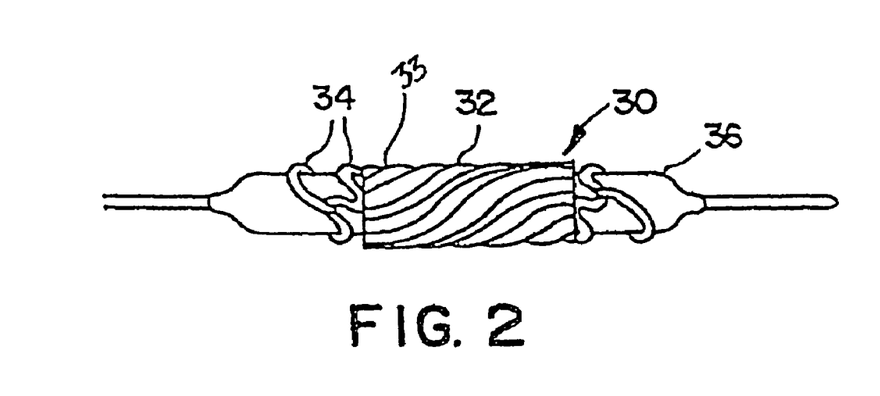
FIG. 2 is an elevational view of another embodiment of a device according to the invention with a balloon catheter as a mode of delivery of the device.

Referring to FIG. 2, an alternative stent 30 is shown. The stent framework 34 is affixed with a film of a porous material 32. This can be accomplished by wrapping the film 32 around the stent framework 34 and securing the film 32 to the framework 34 (i.e., the film is usually sufficiently tacky to adhere itself to the framework but a medical grade adhesive could also be used if needed) so that the film 32 will stay on the balloon 36 and framework 34 until it is delivered to the site of treatment. The film 32 is preferably wrapped over the framework with folds or wrinkles that will allow the stent 30 to be readily expanded into contact with the wall of the lumen to be treated. Alternatively, the film 32 can be molded to the stent framework 34 such that the framework 34 is embedded within the film 32. Preferably, the film 32 is located on a lumen-wall contacting surface 33 of the stent framework 34 such that therapeutic material is substantially locally delivered to a lumen wall, for example, an arterial wall membrane (not shown).

Porous Material

As mentioned above, the device according to the invention is generally a structure including a porous material. In one embodiment, the porous material includes a polymeric film or coating on at least a portion of the structure. In another embodiment, the porous material is an integral portion of the structure. Preferably, the porous material is a biocompatible polymer and is sufficiently tear-resistant and nonthrombogenic. Examples of suitable polymers are disclosed in U.S. Pat. No. 5,679,400 (Tuch). More preferably, the porous material is selected from the group of a natural hydrogel, a synthetic hydrogel, silicone, polyurethane, polysulfone, cellulose, polyethylene, polypropylene, polyamide, polyester, polytetrafluoroethylene, and a combination of two or more of these materials. Examples of natural hydrogels include fibrin, collagen, elastin, and the like. In materials which do not include pores in their usual structural configurations, pores of about 10 micrometers in diameter or as large as 1000 micrometers in diameter can be introduced by conventional means such as by introducing a solvent soluble particulate material into the desired structure and dissolving the particulate material with a solvent.

Typically, and preferably, the porous material is in the form of a sheet material or coating of a nonswelling biostable polymer. As used herein, a "nonswelling biostable" or "nonswellable biostable" polymer is one that does not absorb a significant amount of water (i.e., it absorbs less than about 10 weight percent water) and it is not readily degraded in the body. Such nonswelling biostable polymers include, for example, silicone, polyurethane, polysulfone, cellulose, polyethylene, polypropylene, polyamide, polyester, polytetrafluoroethylene, and combinations thereof. If the polymer is biodegradable, the rate at which it degrades is slower than the rate at which the therapeutic agent elutes.

If the porous material is in the form of a porous sheet (i.e., film) or coating, it can be made by a variety of methods. These methods can include, for example, using a solid particulate material (also referred to herein as pore-forming material) that can be substantially removed after the film or coating is formed, thereby forming pores. By using a solid particulate material during film or coating formation, the size of the pores can, to some extent, be controlled by the size of the solid particulate material being used. The particulate material can range from less than about 1 micrometer in diameter to about 1000 micrometers, preferably about 1 micrometer to about 100 micrometers, more preferably about 5 micrometers to about 50 micrometers. For uniformity of pores, the particulate material can be screened through successively finer mesh sieves, e.g., through 100, 170, 270, 325, 400, and 500 mesh analytical grade stainless steel mesh sieves, to produce a desired range of particle sizes.

The particulate material may include inorganic and organic particulate material, including, for example, sodium chloride, lithium chloride, sucrose, glucose, sorbitol, sodium citrate, sodium ascorbate, urea, citric acid, dextran, poly(ethylene glycol), sodium nitroprusside, mannitol, sodium bicarbonate, ascorbic acid, sodium salicylate, or combinations thereof. It will be understood by one of skill in the art that a mixture of different particulate materials can be used if desired. Also, it will be understood by one of skill in the art that because a portion of the particulate material may remain within the film, it is preferred that the solid particulate material be biocompatible.

Typically, the particulate material chosen is less soluble than the polymer in the chosen solvent (e.g., water or an organic solvent) used to deposit or form the polymer. The particulate material may actually be soluble in the solvent; however, to form pores, it only has to be less soluble than the polymer in the solvent of choice. As the solvent is removed from the solution, the pore-forming material will precipitate out of solution and form particles surrounded by the polymer, which is still in solution. The polymer then will come out of solution as more solvent is removed and the particles will be dispersed within the polymer. After the solvent is removed, the particulate material is removed using a liquid in which the polymer is not soluble, thereby forming pores.

In one method according to the present invention, a porous sheet material (e.g., polyurethane sheet material) can be made by dissolving a polymer (e.g., polyether urethane) in an organic solvent (e.g., 1-methyl-'2-pyrrolidone); mixing into the resulting polymer solution a crystalline, particulate material (e.g., sodium chloride, sucrose, etc.) that is not soluble in the solvent; casting the solution with particulate material into a thin film; and then applying a second solvent (e.g., water), to dissolve and remove the particulate material, thereby leaving a porous sheet. Such a method is disclosed in U.S. Pat. Nos. 5,591,227 (Dinh et al.) and 5,599,352 (Dinh et al.).

Preferably, a combination of soluble and insoluble particulate material may be used to create a broader range of pore sizes. The use of a soluble particulate material, such as poly(ethylene glycol), may create small (<2 µm diameter) interconnecting pores that create a solvent path for the removal of the larger (e.g., 50 µm) particles, which may not be in particle-to-particle contact.

A suspension of particulate material may be created by first dissolving the particulate in a solvent, then precipitating the mixture in a solution of polymer in a second solvent in which the particulate is insoluble. For example, an 8% solution of sodium nitroprusside in ethanol can be added with rapid stirring to a 2% solution of polyurethane in tetrahydrofuran. The sodium nitroprusside precipitates to form a suspension of less than about 5 µm particles.

The weight ratio of pore-forming material to polymer in a coating composition may range from about 1:3 to about 9:1, preferably, about 2:1 to about 9:1, although this is not necessarily limiting. In theory, the porosity is limited by the toughness of the polymer.

A smooth coating may be obtained by applying an atomized spray to the stent. The spray should be applied at a rate such that evaporation prevents the accumulation of sufficient liquid to form drips along the stent. A macroscopically smooth surface may also be obtained by keeping the particle size less than about A of the coating or film thickness.

Although films (i.e., sheet materials) for medical devices, particularly stent bodies, according to the present invention can be manufactured separately from the support structure of the medical device and attached to the support structure after formation, preferred methods include forming the films directly on the support structure such that the support structure is at least partially, preferably completely, encapsulated by the film (i.e., sheet material).

Alternatively, medical devices can include a coating of a porous polymer made by spraying a solution of the polymer and particulate material directly on the support. In this way, the coating does not necessarily form a film that encapsulates the device; rather it forms a coating around the structure (e.g., wire) of the device. The geometry of the porous material (coated wires vs. sheets or films) depends on the coating substrate and is largely independent of the pore forming and application methods used. A film can be made by spraying, dipping, or casting, as long as the mandrel is a rod or a flat sheet. The stent wires can be coated by any of these methods as well, although most preferably, they are coated by spraying to prevent droplet formation.

In one such method, which is disclosed in International Publication No. WO 97/07973 (Medtronic, Inc.), a stent is placed on a mandrel. A particulate material is then applied to the mandrel and stent such that it is lightly adhered to the mandrel. The particulate material should be readily soluble in a solvent which will not also dissolve the polymer chosen for the film. For example, crystalline sodium bicarbonate is a water soluble material that can be used as the particulate material. A nonaqueous liquid, preferably a solvent for the polymer film material, can be applied to the mandrel before applying the particulate material in order to retain more of the particulate material on the mandrel. For example, when a polyurethane is to be used for the film material, the solvent 1-methyl-2-pyrrolidinone (NMP) can be used to wet the surface of the mandrel before the application of particulate material. Preferably, the mandrel is completely dusted with the particulate in the portions of the mandrel to be coated with the polymer film. This can be accomplished by dipping the mandrel in NMP, allowing it to drain vertically for a few seconds and then dusting the sodium bicarbonate onto the mandrel while rotating it horizontally until no further bicarbonate particles adhere. Excess particulate material can be removed by gently tapping the mandrel.

Coating with polymer may proceed immediately following application of the particulate material. A polymer is provided in a dilute solution and is applied to the particle-coated stent and mandrel. For example, polyurethane can be dissolved in NMP to make a 10% solution. Gel particles and particulate impurities can be removed from the solution by use of a clinical centrifuge. The polymer solution can be applied by dipping the mandrel into the solution and letting the solvent evaporate. With the solution of polyurethane and NMP, a single dip in the solution can provide a film of adequate thickness. To assist in the formation of communicating passageways through the polymer between the blood-contacting surface and the lumen-contacting surface, additional sodium bicarbonate particles are preferably dusted onto the polymer solution immediately after the dipping operation and before the polymer solution has dried. Excess particulate material can be removed by gently tapping the mandrel. To precipitate and consolidate the polyurethane film on the stent, it can be dipped briefly (about 5 minutes) in water and then rolled gently against a wetted surface, such as a wet paper towel. The stent assembly can then be placed into one or more water baths over an extended period (e.g., 8 hours) to dissolve and remove the sodium bicarbonate. After drying in air at temperatures from about 20° C. to about 50° C., the film then can be trimmed to match the contour of the wire.

In yet another method, a solvent in which the polymer is soluble that is capable of phase separating from the polymer at a reduced temperature can be used to prepare a porous polymer film. In this method, the stent or other medical device is placed in a cavity of a mold designed for forming a film around the stent, similar to that disclosed in U.S. Pat. No. 5,510,077 (Dinh et al.). A solution of the desired polymer, such as polyurethane, dissolved in a solvent, such as dioxane, is added to the mold. The temperature of the solution is then reduced to a temperature at which the solvent freezes and phase separates from the polymer, thereby forming particulate material (i.e., frozen solvent particles) in situ. Typically, for polyurethane in dioxane, this is a temperature of about −70° C. to about 3° C. The composition is then immersed in an ice cold water bath (at about 3° C.) for a few days to allot the dioxane to dissolve into the ice cold water, thereby forming pores. The number and size of the pores can be controlled by the concentration of the polymer and the freezing temperature. A method similar to this is disclosed in Liu et al., J. Biomed. Mater. Res., 26, 1489 (1992). This method can be improved on by using a two-step freezing process as disclosed in U.S. Pat. Application Ser. No. 09/069,659, filed on Apr. 29, 1998.

In yet another embodiment, a porous material can be created from a mixture of a low boiling good solvent and a higher boiling poor solvent, in which the polymer is soluble. After application to the target substrate, the lower boiling good solvent evaporates preferentially until a point is reached where the polymer precipitates from the remaining solvent mixture, which is relatively richer in the poor solvent. The polymer precipitates in and around pockets of the poor solvent, creating a porous structure. The number and size of pores can be controlled by the boiling points of the two solvents, the concentration of polymer and the drying rate. An example is a 1% solution of poly(1-lactic acid) (PLLA) in a 60:40 mixture of chloroform:iso-octane. As the chloroform evaporates, the PLLA precipitates from the iso-octane to create an opaque PLLA coating containing 2-5 μm pores. This method is further described in U.S. Pat. No. 5,679,400 (Tuch).

Therapeutic Agent

The therapeutic agent used in the present invention could be virtually any therapeutic agent which possesses desirable therapeutic characteristics and which can be provided in a form that can be solubilized, for example, by water or an organic solvent, and are capable of being eluted from the porous polymeric material in the body of a patient. Preferred therapeutic agents are solids, gels, or neat liquids (i.e., materials not dissolved in a solvent) at room temperature (i.e., about 20-25° C.), and preferably at body temperatures, that are capable of being eluted from the porous polymeric material in the body of a patient. For example, antithrombotics, antiplatelet agents, antimitotic agents, antioxidants, antimetabolite agents, anti-inflammatory agents, enzyme inhibitors, and anti-angiogenic factors as disclosed in U.S. Pat. No. 5,716,981 (Hunter et al.) could be used. Anticoagulant agents, such as heparin, heparin derivatives, and heparin analogs, could also be used to prevent the formation of blood clots on the device.

Methods of Making an Implantable Device

A structure having a porous material, preferably a porous polymeric material, can be loaded with one or more therapeutic agents using a wide variety of methods. For example, the porous material can be immersed in a solution or dispersion of the therapeutic agent in a solvent. The solution (preferably, a supersaturated solution) or dispersion is allowed to fill the pores and the solvent is allowed to evaporate leaving the therapeutic agent dispersed within at least a portion of the pores. The solvent can be water or an organic solvent that does not dissolve the polymer. If the solvent does not dissolve the therapeutic agent, the particles of the therapeutic agent are smaller than the pore openings. Alternatively, in certain embodiments, the solvent can be chosen such that it swells the polymer, thereby achieving a greater level of incorporation of the therapeutic agent.

The following methods for loading one or more therapeutic agents into porous material are improved over prior art methods, such as spray coating methods. Although the same amount of therapeutic agent can be loaded onto a medical device, significantly less (e.g., about 100× less) waste of the therapeutic agent occurs using the following methods. This is particularly important for expensive therapeutic agents, such as peptic drugs.

In one embodiment of the invention, filling of the pores can be enhanced through the use of ultrasonics, vacuum, and/or pressure. While the device is submerged in solution, ultrasonic energy or vacuum can be used to accelerate the removal of air bubbles from the pores allowing the pores to fill with the solution containing the therapeutic agent. Hyperbaric pressure on the solution may cause the air in the pores to be dissolved in the solution, thereby allowing the pores to fill with liquid. Furthermore, the level of incorporation can be increased by using multiple dip-vacuum-dry cycles. If the therapeutic agent saturates the solution by 10% by volume, for example, when the solvent evaporates the pores will be 10% filled with the agent. Repeating the cycle will fill the remaining 90% void space and fill an additional 9% of the original pore volume. Further cycles continue the trend. For this procedure to be effective, however, the solution is saturated so that the previously deposited agent does not dissolve in subsequent cycles.

Preferably, a method of the invention includes loading a structure comprising a porous material with a concentrating agent, which may be a precipitating agent (e.g., a binding agent, sequestering agent, nucleating agent, etc.), a seed crystal, or the like, dispersed throughout at least a portion, preferably, a substantial portion, of the porous material, and subsequently loading the structure comprising a porous material and the concentrating agent with a solution of a therapeutic agent, wherein the therapeutic agent is removed from solution (e.g., as by crystallization and/or precipitation) within the porous material at the locations of the concentrating agent. This is a significantly improved method in that the concentrating agent provides a driving force for localization of the drug within the pores of the polymer. That is, it is believed that the concentrating agent provides a thermodynamically favorable surface for crystallization or precipitation.

The concentrating agent can be a precipitating agent or a seed crystal, for example, or any substance that can cause the therapeutic agent to fall out of solution. As used herein, a seed crystal is a solid material that is the same as the therapeutic agent being deposited. As used herein, a precipitating agent is a solid material that is different from the therapeutic agent being deposited. It can include, for example, materials that have a particular affinity for the therapeutic agent of interest, such as binding agents, sequestering agents, nucleating agents, and mixtures thereof. Examples of sequestering agents include heparin to sequester heparin binding growth factors such as bFGF and, for example, cyclodextrins to trap appropriately sized therapeutic agents to fit in their ring structures. Examples of binding agents include polycations (e.g., protamine) and polyanions (e.g., heparin sulfate) for binding anionic and cationic therapeutic agents, respectively. The binding agent can also include a counterioh of a salt that is insoluble upon complexation with the therapeutic agent in the solvent used in the solution of the therapeutic agent.

The solution containing the therapeutic agent is preferably a supersaturated solution, although this is not a necessary requirement. This can be prepared at elevated temperatures taking into consideration the limits of stability of the therapeutic agents and the porous material. The porous polymeric material with concentrating agent therein can be immersed in a solution of the therapeutic agent in a solvent. The solution is allowed to fill the pores and the therapeutic agent allowed to come out of solution (e.g., as by the formation of crystals). The solvent can be water or an organic solvent that does not dissolve the porous polymer, although it may swell the polymer as described above. The choice of solvent is one that is compatible with the therapeutic agent and porous material of choice. Filling of the pores can be enhanced through the use of ultrasonics, vacuum, and/or pressure, as well as by using multiple dip-vacuum-dry cycles, as described above.

Crystal and/or precipitate formation can be initiated by a variety of mechanisms. They may spontaneously form. Alternatively, the solution of the therapeutic agent within the pores may need to be cooled to initiate crystallization and/or precipitation. It may be possible to initiate crystallization and/or precipitation by changing the pH and/or ionic strength of the solution of the therapeutic agent within the pores.

The initial concentrating agent, which may be a solid, liquid, or a gel, can be placed in the pores of the porous material by a variety of methods. For example, if the concentrating agent is a seed crystal of the therapeutic agent of interest, immersing the porous material in a solution or dispersion of the therapeutic agent in a solvent, allowing it to fill the pores, and allowing the solvent to evaporate, provides the therapeutic agent dispersed within at least a portion of the pores, as described above. Similarly, if the concentrating agent is a precipitating agent, the porous material can be immersed in a solution of this agent.

The methods of the present invention are advantageous in that the structure can be loaded with the therapeutic agent in situ, i.e., at or near the point of therapeutic use, typically before administration, preferably implantation, to a patient. This is particularly useful because the device can be stored and transported prior to incorporation of the therapeutic agent. This feature has several advantages. For example, the relevant consumer can select the therapeutic agent to be used from a wider range of therapeutic agents. Thus, the therapeutic agent selected is not limited to only those supplied with the device but can instead be applied according to the therapy required.

In order to provide additional control over the elution of the therapeutic agent, an overlayer may be applied to the medical device, as is disclosed in U.S. Pat. Nos. 5,679,400 (Tuch), 5,624,411 (Tuch), and 5,624,411 (Tuch). The overlayer, typically in the form of a porous polymer, is in intimate contact with the therapeutic agent and allows it to be retained on the medical device. It also controls the administration of the therapeutic agent following implantation. For a stent, an overlayer is particularly desirable to retain the therapeutic agent on the stent during expansion of the stent. Thus, the present invention also relates to a method for making an intravascular stent. The underlying structure of the stent can be virtually any stent design, whether of the self-expanding type or of the balloon-expandable type and whether metal or polymeric. Thus metal stent designs such as those disclosed in U.S. Pat. No. 4,733,665 issued to Palmaz, U.S. Pat. No. 4,800,882 issued to Gianturco or U.S. Pat. No. 4,886,062 issued to Wiktor could be used in the present invention. The stent could be made of virtually any bio-compatible material having physical properties suitable for the design. For example, tantalum and stainless steel have been proven suitable for many such designs and could be used in the present invention. Also, stents made with biostable or bioabsorbable polymers such as poly(ethylene terephthalate), polyacetal, poly(lactic acid), poly(ethylene oxide)/poly(butylene terephthalate) copolymer could be used in the present invention. Although the stent surface should be clean and free from contaminants that may be introduced during manufacturing, the stent surface requires no particular surface treatment in order to retain the coating applied in the present invention. Both the inner and outer surfaces of the stent may be provided with the coating according to the present invention.

In order to provide the coated stent according to the present invention, a solution which includes a solvent, a polymer dissolved in the solvent and a therapeutic substance dispersed in the solvent is first prepared. It is important to choose a solvent, a polymer and a therapeutic substance that are mutually compatible. It is essential that the solvent is capable of placing the polymer into solution at the concentration desired in the solution. It is also essential that the solvent and polymer chosen do not chemically alter the therapeutic character of the therapeutic substance. However, the therapeutic substance only needs to be dispersed throughout the solvent so that it may be either in a true solution with the solvent or dispersed in fine particles in the solvent. Examples of some suitable combinations of polymer, solvent and therapeutic substance are set forth in Table 1 below.

TABLE 1

| POLYMER | SOLVENT | THERAPEUTIC SUBSTANCE |
|---|---|---|
| poly(L-lactic acid) | chloroform | dexamethasone |
| poly(lactic acid-co-glycolic acid) | acetone | dexamethasone |
| polyether urethane | N-methyl pyrrolidone | tocopheral (vitamin E) |
| silicone adhesive | xylene | dexamethasone phosphate |
| poly(hydroxy-butyrate-co-hydroxyvalerate) | dichloro-methane | aspirin |
| fibrin | water (buffered saline) | heparin |

The solution is applied to the stent and the solvent is allowed to evaporate, thereby leaving on the stent surface a coating of the polymer and the therapeutic substance. Typically, the solution can be applied to the stent by either spraying the solution onto the stent or immersing the stent in the solution. Whether one chooses application by immersion or application by spraying depends principally on the viscosity and surface tension of the solution, however, it has been found that spraying in a fine spray such as that available from an airbrush will provide a coating with the greatest uniformity and will provide the greatest control over the amount of coating material to be applied to the stent. In either a coating applied by spraying or by immersion, multiple application steps are generally desirable to provide improved coating uniformity and improved control over the amount of therapeutic substance to be applied to the stent.

The polymer chosen must be a polymer that is biocompatible and minimizes irritation to the vessel wall when the stent is implanted. The polymer may be either a biostable or a bioabsorbable polymer depending on the desired rate of release or the desired degree of polymer stability, but a bioabsorbable polymer is probably more desirable since, unlike a biostable polymer, it will not be present long after implantation to cause any adverse, chronic local response. Bioabsorbable polymers that could be used include poly(L-lactic acid), polycaprolactone, poly(lactide-co-glycolide), poly(hydroxybutyrate), poly(hydroxybutyrate-co-valerate), polydioxanone, polyorthoester, polyanhydride, poly(glycolic acid), poly(D,L-lactic acid), poly(glycolic acid-co-trimethylene carbonate), polyphosphoester, polyphosphoester urethane, poly(amino acids), cyanoacrylates, poly(trimethylene carbonate), poly(iminocarbonate), copoly(ether-esters) (e.g. PEO/PLA), polyalkylene oxalates, polyphosphazenes and biomolecules such as fibrin, fibrinogen, cellulose, starch, collagen and hyaluronic acid. Also, biostable polymers with a relatively low chronic tissue response such as polyurethanes, silicones, and polyesters could be used and other polymers could also be used if they can be dissolved and cured or polymerized on the stent such as polyolefins, polyisobutylene and ethylene-alphaolefin copolymers; acrylic polymers and copolymers, vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile, polyvinyl ketones; polyvinyl aromatics, such as polystyrene, polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as Nylon 66 and polycaprolactam; alkyd resins; polycarbonates; polyoxymethylenes; polyimides; polyethers; epoxy resins, polyurethanes; rayon; rayon-triacetate; cellulose, cellulose acetate, cellulose butyrate; cellulose acetate butyrate; cellophane; cellulose nitrate; cellulose propionate; cellulose ethers; and carboxymethyl cellulose.

The ratio of therapeutic substance to polymer in the solution will depend on the efficacy of the polymer in securing the therapeutic substance onto the stent and the rate at which the coating is to release the therapeutic substance to the tissue of the blood vessel. More polymer may be needed if it has relatively poor efficacy in retaining the therapeutic substance on the stent and more polymer may be needed in order to provide an elution matrix that limits the elution of a very soluble therapeutic substance. A wide ratio of therapeutic substance to polymer could therefore be appropriate and could range from about 10:1 to about 1:100.

The therapeutic substance used in the present invention could be virtually any therapeutic substance which possesses desirable therapeutic characteristics for application to a blood vessel. This can include both solid substances and liquid substances. For example, glucocorticoids (e.g. dexamethasone, betamethasone), heparin, hirudin, tocopherol, angiopeptin, aspirin, ACE inhibitors, growth factors, oligonucleotides, and, more generally, antiplatelet agents, anticoagulant agents, antimitotic agents, antioxidants, antimetabolite agents, and anti-inflammatory agents could be used. Antiplatelet agents can include drugs such as aspirin and dypyridamole. Aspirin is classified as an analgesic, antipyretic, anti-inflammatory and antiplatelet drug. Dypridimole is a drug similar to aspirin in that it has anti-platelet characteristics. Dypridimole is also classified as a coronary vasodilator. Anticoagulant agents can include drugs such as heparin, coumadin, protamine, hirudin and tick anticoagulant protein. Antimitotic agents and antimetabolite agents can include drugs such as methotrexate, azathioprine, vincristine, vinblastine, fluorouracil, adriamycin and mutamycin.

The following nonlimiting examples will further illustrate the invention. All parts, percentages, ratios, etc. are by weight unless otherwise indicated.

EXAMPLES

Example 1

Wiktor stents were coated as follows: 4 grams of a 5 wt % solution of polyurethane as disclosed in U.S. Pat. No. 4,873,308 (Coury et al.) in tetrahydrofuran (THF) and 20 grams of a 5 wt % solution of citric acid in THF were combined and sprayed onto wiktor stents using an air brush, similar to the method disclosed in U.S. Pat. No. 5,679,400 (Tuch). Citric acid was extracted with deionized water for 10 minutes. The stent was then air dried at ambient temperature and weighed. The porous polyurethane coating weights, were 0.5-0.7 mg.

Into a microcentrifuge tube was added 0.12 g tissue factor pathway inhibitor. (TFPI) and 1.0 ml sterile water. This was agitated to dissolve the TFPI. The polyurethane coated stents were immersed in the TFPI solution, which was subjected to reduced pressure (28 inches of Hg) to evacuate the air from the pores. The stents were air dried and the immersion/vacuum process was repeated twice. After the last immersion process, stents were air dried at ambient temperature for 20 minutes. Each stent was immersed for less than two seconds in deionized water to remove TFPI on the surface of the stents. The stents were then dried in ambient temperature under vacuum for about 12 hours. The stents were weighed to determine the amount of TFPI loaded into the pores, which ranged from 0.15 mg to 0.33 mg.

Half the stents were overcoated with a 2 wt % solution of polyurethane solution in THF using the spray coating method described above, resulting in a coating weight of 0.6 mg. These stents were tested for elution. The stents with the overcoating eluted more slowly than the stents without the overcoating.

Example 2

A 1% solution of dexamethasone in acetone was made, forming a clear solution. The solution was placed in an airbrush reservoir (Badger #200). Wiktor type tantalum wire stents were sprayed with the solution in short bursts while rotating the stents. The acetone quickly evaporated from the stents, leaving a white residue on the stent wire. The process was continued until all of the stent wires were coated. The drug elution rate for the stent was determined by immersing the stent in phosphate buffered saline solution (pH=7.4). Traces of dexamethasone were observed to remain on the immersed stents for less than 31 hours.

Example 3

A 2% solution of dexamethasone in acetone was made, forming a solution with suspended particles of dexamethasone. The solution was placed into a tube. Wiktor type tantalum wire stents were dipped rapidly and were allowed to dry. Each stent was dipped into the solution 12-15 times to provide a white surface coating. Two stents were placed on an angioplasty balloon and were inflated on the balloon. Approximately 80% of the dexamethasone coating flaked off of the stents.

Example 4

A solution of 1% dexamethasone and 0.5% poly(caprolactone) (Aldrich 18, 160-9) in acetone was made. The solution was placed into a tube. Wiktor type tantalum wire stents were dipped rapidly and were allowed to dry. Each stent was dipped into the solution 12-15 times to provide a white surface coating. A stent so coated was expanded on a 3.5 mm angioplasty balloon causing a significant amount of the coating to become detached.

Example 5

A solution of 1% dexamethasone and 0.5% poly(L-lactic acid) (Medisorb) in acetone was made. The solution was placed into a tube. Wiktor type tantalum wire stents were dipped rapidly and were allowed to dry. Each stent was dipped into the solution 12-15 times to provide a white surface coating. A stent so coated was expanded on a 3.5 mm angioplasty balloon causing only a small portion of the coating (less than 25%) to become detached)

Example 6

A solution including a 2% dispersion of dexamethasone and a 1% solution of poly(L-lactic acid) (CCA Biochem MW=550,000) in chloroform was made. The solution was placed into an airbrush (Badger). Wiktor type tantalum wire stents were sprayed in short bursts and were allowed to dry. Each stent was sprayed with the solution about 20 times to provide a white surface coating. A stent so coated was expanded on a 3.5 mm angioplasty balloon. The coating remained attached to the stent throughout the procedure.

Example 7

Figure 3:
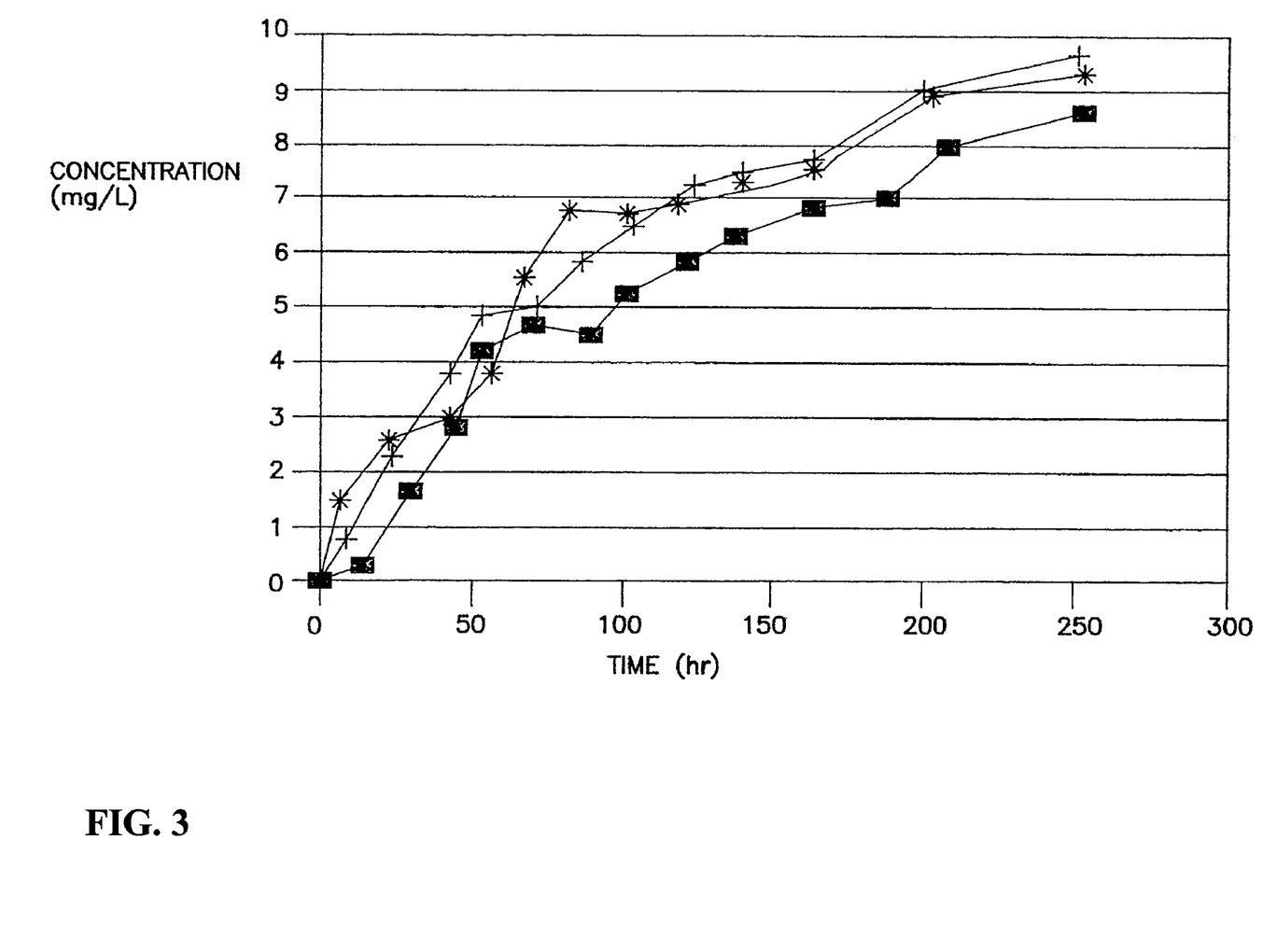
FIG. 3 is a plot showing elution profiles for stents according to the present invention with a coating of dexamethasone and poly(L-lactic acid) made according to Example 7.

A solution including a 2% dispersion of dexamethasone and a 1% solution of poly(L-lactic acid) (CCA Biochem MW=550,000) in chloroform was made. The solution was placed into an airbrush (Badger #250-2). Wiktor type tantalum wire stents were suspended from a fixture and sprayed in 24 short bursts (6 bursts from each of the four directions perpendicular to the stent axis) and were allowed to dry. The resulting stents had a coating weight of about 0.0006-0.0015 grams. Three of the stents were tested for long term elution by placing one stent in 3.0 ml of phosphate buffered saline solution (pH=7.4) at room temperature without stirring. The amount of dexamethasone eluted was evaluated by measuring absorbance at 244 nm in a UV-VIS spectrophotometer. The results of this test are given in FIG. 3.

Example 8

Figure 4:
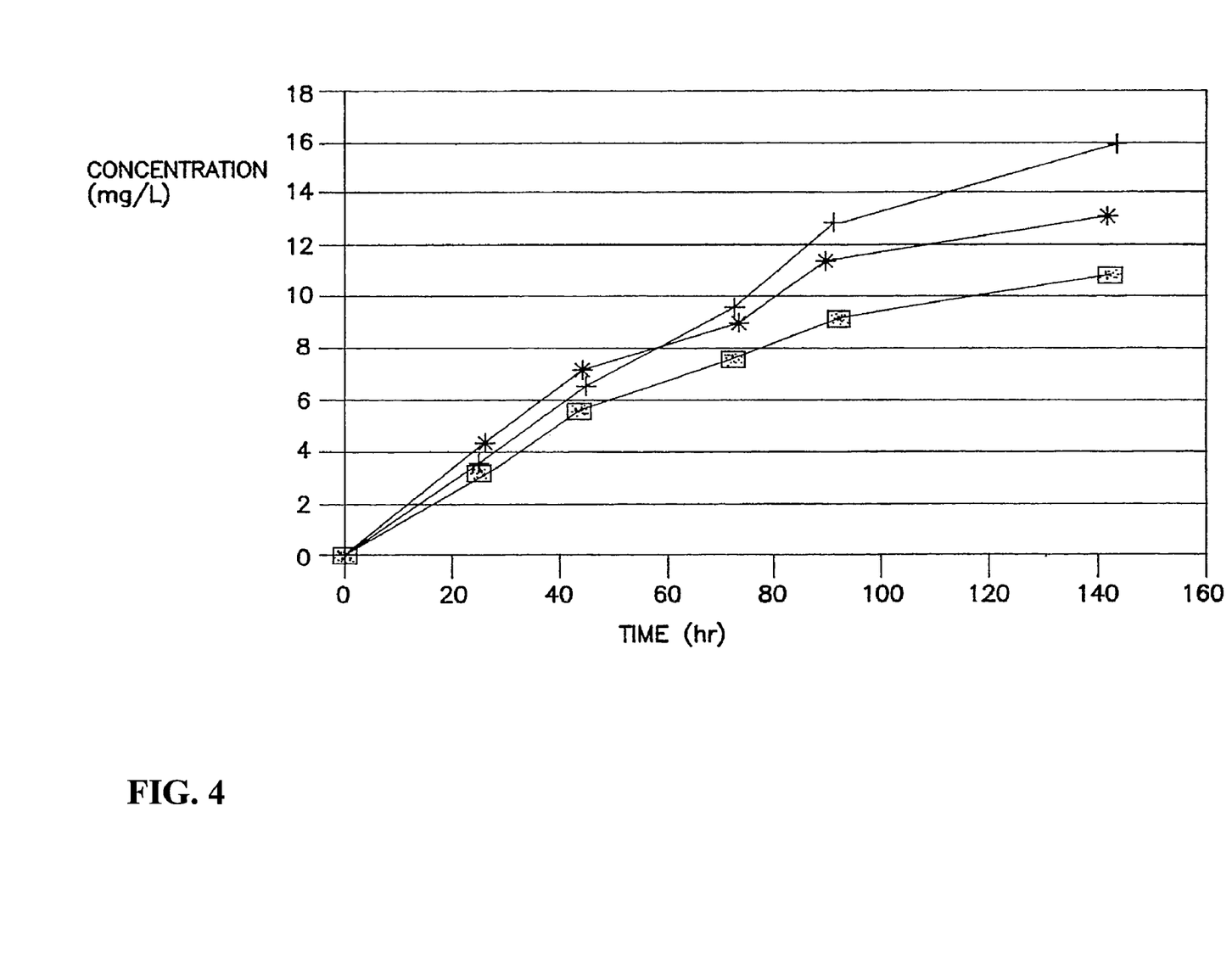
FIG. 4 is a plot showing elution profiles for sterilized stents according to the present invention with a coating of dexamethasone and poly(L-lactic acid) made according to Example 8.

A solution including a 2% dispersion of dexamethasone and a 1% solution of poly(L-lactic acid) (Medisorb 100-L) in chloroform was made along with a control solution of 1% of poly(L-lactic acid) (Medisorb 100-L) in chloroform. The solutions was placed into an airbrush (Badger #250-2). Wiktor type tantalum wire stents were expanded on a 3.0 mm balloon, suspended from a fixture and sprayed in 16 short bursts (2-3 bursts of about 1 second followed by several minutes drying time between applications). The resulting dexamethasone-coated stents had an average coating weight of about 0.0012 grams while the polymer-coated stents had an average polymer weight of about 0.0004 grams. The stents were sterilized in ethylene oxide. Three of the sterilized dexamethasone-coated stents were tested for long term elution by placing one stent in 3.0 ml of phosphate buffered saline solution (pH=7.4) at room temperature without stirring. The amount of dexamethasone eluted was evaluated by measuring absorbance at 244 nm in a UV-VIS spectrophotometer. The results of this test are given in FIG. 4. Dexamethasone-coated stents and polymer-coated control stents were implanted in the coronary arteries of 8 pigs (N=12 for each type) according to the method set forth in "Restenosis After Balloon Angioplasty—A Practical Proliferative Model in Porcine Coronary Arteries," by Robert S. Schwartz, et al, Circulation 82(6): 2190-2200, December 1990, and "Restenosis and the Proportional Neointimal Response to Coronary Artery Injury: Results in a Porcine Model" by Robert S. Schwartz et al, *J Am Coll Cardiol;* 19; 267-74 Feb. 1992 with the result that when compared with the controls, the dexamethasone-coated stents reduced the amount of proliferation associated with the arterial injury.

The complete disclosures of all patents, patent applications, and publications referenced herein are incorporated herein by reference as if individually incorporated. Various modifications and alterations of this invention will become apparent to those skilled in the art without departing from the scope and spirit of this invention, and it should be understood that this invention is not to be unduly limited to illustrative embodiments set forth herein.

We claim:

1. A method for making an intravascular stent comprising the steps of:
   (a) providing a radially expandable stent body;
   (b) applying to the stent body a mixture of a solvent, a polymer, and a therapeutic substance;
   (c) evaporating the solvent; and
   (d) repeating application and evaporating steps (b) and (c) to provide an amount of polymer and therapeutic substance on the stent body,
      wherein the stent body retains the polymer and therapeutic substance when the stent body is radially expanded.

2. The method according to claim 1, wherein the stent body has a metal surface.

3. The method according to claim 1, wherein the mixture is applied to the stent body by spraying.

4. The method according to claim 1, wherein the mixture is applied to the stent body by dipping.

5. The method according to claim 1, wherein the polymer is selected from the group consisting of silicones, polyurethanes, polyesters, vinyl homopolymers and copolymers, acrylate homopolymers and copolymers, polyethers and cellulosics.

6. The method according to claim 1, wherein the ratio of therapeutic substance to polymer in the mixture is in the range of about 10:1 to 1:100.

7. The method according to claim 1, wherein the therapeutic substance is selected from the group consisting of glucocorticoids, dexamethasone, dexamethasone sodium phosphate, anticoagulants, heparin, hirudin, tick anticoagulant peptide, angiopeptin, antimitotic agents, and oligonucleotides.

8. A method for making an intravascular stent having a radially expandable stent body with a mixture of a solvent, a polymer, and a therapeutic substance applied thereto, and the stent body retains the polymer and therapeutic substance when the stent body is radially expanded, said method of making comprising the steps of:
   (a) providing the radially expandable stent body;
   (b) applying to the stent body the mixture of the solvent, the polymer, and the therapeutic substance;
   (c) evaporating the solvent; and
   (d) repeating application and evaporating steps (b) and (c) to provide an amount of polymer and therapeutic substance on the stent body.

9. The method according to claim 8, wherein the stent body has a metal surface.

10. The method according to claim 8, wherein the stent body is balloon expandable.

11. The method according to claim 8, wherein the mixture is applied to the stent body by spraying.

12. The method according to claim 8, wherein the mixture is applied to the stent body by dipping.

13. The method according to claim 8, wherein the polymer is selected from the group consisting of silicones, polyurethanes, polyesters, vinyl homopolymers and copolymers, acrylate homopolymers and copolymers, polyethers and cellulosics.

14. The method according to claim 8, wherein the ratio of therapeutic substance to polymer in the mixture is in the range of about 10:1 to 1:100.

15. The method according to claim 8, wherein the therapeutic substance is selected from the group consisting of glucocorticoids, dexamethasone, dexamethasone sodium phosphate, anticoagulants, heparin, hirudin, tick anticoagulant peptide, angiopeptin, antimitotic agents, and oligonucleotides.

16. A method for making an intravascular stent having a cylindrical, balloon expandable metal stent body with a mixture of a solvent, a polymer, and a therapeutic substance applied thereto, and the stent body retains the polymer and therapeutic substance when the stent body is radially expanded, said method comprising the steps of:
   (a) providing the cylindrical, balloon expandable metal stent body;
   (b) spraying onto the stent body the mixture of the solvent, the polymer, and therapeutic substance;
   (c) evaporating the solvent; and
   (d) repeating application and evaporating steps (b) and (c) to provide an amount of polymer and therapeutic substance on the stent body.

17. The method according to claim 16, wherein the polymer is selected from the group consisting of silicones, polyurethanes, polyesters, vinyl homopolymers and copolymers, acrylate homopolymers and copolymers, polyethers and cellulosics.

18. The method according to claim 16, wherein the ratio of therapeutic substance to polymer in the mixture is in the range of about 10:1 to 1:100.

19. The method according to claim 16, wherein the therapeutic substance is selected from the group consisting of glucocorticoids, dexamethasone, dexamethasone sodium phosphate, anticoagulants, heparin, hirudin, tick anticoagulant peptide, angiopeptin, antimitotic agents, and oligonucleotides.

* * * * *